United States Patent [19]

Hirata et al.

[11] 4,283,408

[45] Aug. 11, 1981

[54] GUANIDINOTHIAZOLE COMPOUNDS, PROCESS FOR PREPARATION AND GASTRIC INHIBITING COMPOSITIONS CONTAINING THEM

[75] Inventors: Yasufumi Hirata, Omiya; Isao Yanagisawa, Tokyo; Yoshio Ishii, Omiya; Shinichi Tsukamoto, Tokyo; Noriki Ito, Twatsuki; Yasuo Isomura, Yokohama; Masaaki Takeda, Urawa, all of Japan

[73] Assignee: Yamanouchi Pharmaceutical Co., Ltd., Tokyo, Japan

[21] Appl. No.: 107,629

[22] Filed: Dec. 27, 1979

[30] Foreign Application Priority Data

Aug. 2, 1979 [JP] Japan .................. 54-98906

[51] Int. Cl.³ .............. C07D 277/38; A61K 31/425
[52] U.S. Cl. .................. 424/270; 548/193; 548/196; 548/197
[58] Field of Search ............ 548/197; 424/270

[56] References Cited

U.S. PATENT DOCUMENTS

| | | | |
|---|---|---|---|
| 3,950,333 | 4/1976 | Durant et al. | 548/197 |
| 4,165,377 | 8/1979 | Jones et al. | 548/197 |
| 4,165,378 | 8/1979 | Gilman | 548/197 |

OTHER PUBLICATIONS

Miyazaki et al., Chem. Ab 48, 8259h.
Knott, J. Chem. Soc. 1945, 686.
Cooper et al., J. Chem. Soc. 1952, 5036.

*Primary Examiner*—Mark L. Berch
*Attorney, Agent, or Firm*—Burgess, Ryan and Wayne

[57] ABSTRACT

Novel guanidinothiazole compounds of the general formula

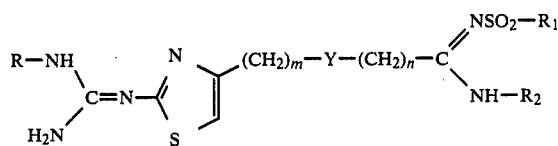

wherein R represents a hydrogen atom or a lower alkyl group, $R_1$ represents an amino group, a lower alkyl group, a halogeno lower alkyl group, a substituted- or unsubstituted-aryl group, a mono- or di-lower alkylamino group, an arylamino group or an aralkylamino group, $R_2$ represents a hydrogen atom, a lower alkyl group, a lower alkenyl group or a lower alkynyl group, Y represents a sulfur atom or a methylene group, m and n, each represents an integer of 1-3, and the pharmacologically acceptable acid addition salts thereof, they are useful as gastric acid secretion inhibitors.

6 Claims, No Drawings

GUANIDINOTHIAZOLE COMPOUNDS, PROCESS FOR PREPARATION AND GASTRIC INHIBITING COMPOSITIONS CONTAINING THEM

DETAILED EXPLANATION OF THE INVENTION

The present invention relates to novel guanidinothiazole compounds useful as gastric acid secretion inhibitors, the process for preparing them and the medical compositions containing them.

Thus, according to this invention, there are provided novel guanidinothiazole compounds of general formula

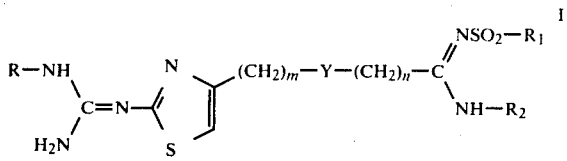

wherein R represents a hydrogen atom or a lower alkyl group, $R_1$ represents an amino group, a lower alkyl group, a halogeno lower alkyl group, a substituted- or unsubstituted-aryl group, a mono- or di-lower alkylamino group, an arylamino group or an aralkylamino group, $R_2$ represents a hydrogen atom, a lower alkyl group, a lower alkenyl group or a lower alkynyl group, Y represents a sulfur atom or a methylene group, m and n, each represents an integer of 1–3, and the acid addition salts thereof capable being supplied for medical purposes.

Furthermore, according to other embodiments of this invention, there are provided process for preparing the novel guanidinothiazole compounds of general formula I and the medical compositions containing said guanidinothiazole compounds.

The term "lower" in the above definition means a straight or branched carbon chain having 1–5 carbon atoms. Therefore, as a lower alkyl group, there are a methyl group, an ethyl group, an isopropyl group, a butyl group, etc.; as a lower alkenyl group, there are a vinyl group, an allyl group, an isopropenyl group, etc.; as a lower alkynyl group, there are an ethynyl group, a propynyl group, a butynyl group, etc. Further, as an aralkyl group, there are a benzyl group, a phenethyl group, etc.; as an aryl group, there are a phenyl group, a naphthyl group, etc. This aryl group may have a substituent such as a halogen atom, a hydroxyl group, an amino group, an alkoxy group, etc.

Furthermore, the compounds of general formula I easily form acid addition salts thereof and there also exist the tautomers thereof. Therefore, the invention includes also the acid addition salts and the tautomers thereof.

As mentioned above, the guanidinothiazole compounds of this invention readily form acid addition salts capable of being used for medical purposes. As these salts, there are the salts of the guanidinothiazole compounds with inorganic acids or organic acids. Examples of the inorganic acid salts are hydrochlorides, hydrobromides, sulfates, etc. Also, examples of the particularly useful organic acid salts are the salts with aliphatic carboxylic acids such as acetic acid, maleic acid, fumaric acid, etc.

It is the first feature of this invention that the compounds provided by this invention have a gastric acid secretion inhibitory activity and this activity is not caused by an anticholinergic activity. Since conventional commercially available gastric acid secretion inhibitors are mostly based on the anticholinergic activity and unwanted side effects caused by the anticholinergic activity have been pointed out, the compounds of this invention are useful as new type gastric acid secretion inhibitors.

It is the second feature of this invention that the compounds of this invention have an activity for inhibiting gastric acid secretion through a histamine $H_2$-receptor. It has been proposed to classify histamine receptors into $H_1$-receptors and non $H_1$-receptors or $H_2$-receptors by Ash and Schild; "Brit. J. of Pharmacol. Chemother," 27, 427(1966) and Black et al.; "Nature," 236, 385(1972). The effects of histamine on gastric acid secretion and heart rate in isolated guinea pig atrium are mediated by the $H_2$-receptor and these histamine effects are not inhibited by conventional antihistamines such as mepyramine but are antagonized by blockers of $H_2$-receptors such as metiamide.

Since a histamine $H_2$-receptor blocking agent has an activity for inhibiting the basic secretion of gastric acid and the gastric acid secretion induced by gastrin histamine, methacholine or food, it can be used for the treatment of gastric ulcer and duodenal ulcer caused by the hypersecretion of gastric acid.

Hitherto, as the materials possessing the features as in the compounds of this invention, the compounds in Belgian Pat. Nos. 804,145; 866,156; 867,105; 867,594 and U.S. Pat. No. 3,950,333, etc., are known but the compounds of this invention are all novel compounds having different structures and more superior pharmacological effects compared with those of the known compounds.

The compounds of this invention can be administered orally or parenterally but the oral administration is preferred. The compounds of this invention are used as the free bases or the pharmacologically acceptable salts thereof and, in general, they are used as medical or pharmaceutical compositions with carriers or diluents which can be used generally for preparing medicaments. In the case of oral administration, it is most convenient to use the medical compositions of this invention in the form of capsules or tablets but they may be used as sustained release preparations. Furthermore, the compositions may be used as sugar-coated preparations or syrups. The doses thereof at oral administration are 50 to 800 mg per day and it is proper to administer the medicament in 1 to 4 divided doses.

The compounds of this invention shown by general formula I are inhibitors for gastric acid secretion having low toxicity which were proved by the following tests:

(i) Gastric acid secretion in anesthetized dogs:

Mongrel dogs weighing 8 to 15 Kg were deprived of food for 24 hr and anesthetized intravenously with pentobarbital (30 mg/Kg). A stainless steel cannula was introduced through the ventral wall of the stomach after ligation of the pylorus and esophagus (Okabe, S. et al.: Japan J. Pharmacol. 27, 17–22, 1977). The gastric juice was collected from the gastric cannula by gravity drainage every 15 min. Test compounds were given intravenously after gastric secretion induced by a continuous intravenous infusion of histamine (160 μg/Kg-hr) reached a steady state. The acidity of gastric juice was measured by titration with 0.05 N NaOH using an automatic titrator (Kyoto Electronics Manufacturing Co., AT-107). The percent inhibition of gastric secretion by each dose of drugs was calculated from the difference between the pr drug acid output and the minimum acid output which was usually obtained within 45 min after drug administration. The dose producing 50% inhibition of the acid output was obtained from the dose-response curve in which the inhibition was semilogarithmically plotted against dose. The data are shown in Table I, under column entitled (A).

(ii) Gastric acid secretion in pylorus-ligated rats

Male Wister rats weighing about 200 g were deprived of food for 24 hr but allowed free access to water prior to the experiments in individual cages. The pylorus was ligated under ether anesthesia according to the method of Shay et al. (Gastroenterol. 5, 43–61, 1945). Test compounds were intraduodenally given immediately after the ligation of pylorus. The animals were sacrificed 4 hr after drug administration and gastric contents were collected. The acidity of gastric juice was measured by titration with 0.05 N NaOH using an automatic titrator (Kyoto Electronics Manufacturing Co., AT-107). The percent inhibition of gastric secretion by each dose of drugs was calculated from the acid outputs of control and of treated groups. $ED_{50}$ values were determined by the probit method. The data are shown in Table I, under column entitled (B).

(iii) Acute toxicity in mice

Drugs were injected intravenously in male ICR mice weighing about 35 g at a rate of 0.1 ml/10 sec and the animals were kept under observation for 7 days. $LD_{50}$ values were determined by up and down method using 10 animals. The data are shown in Table I, under column entitled (C).

The guanidinothiazole compounds of this invention shown by general formula I can be produced by the following processes.

Production process 1:

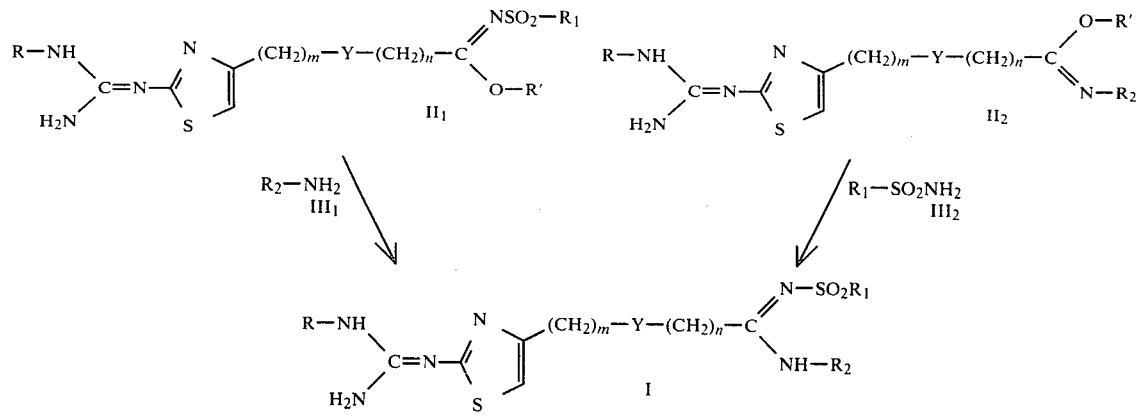

In the above formulae, R' represents a lower alkyl group, and R, $R_1$, $R_2$, Y, m and n have the same significance as above.

This process is performed either by reacting the starting material compound of formula $II_1$ and a reactive amount of the amine of formula $III_1$, or by reacting the starting material compound of formula $II_2$ and a reactive amount of the amine of formula $III_2$. The amines shown by formula $III_1$ or $III_2$ used in the processes are those which are capable to produce the desired product I by the reaction with the starting material compound $II_1$ or $II_2$.

Examples of the compounds of formula $III_1$ are ammonia (ammonium chloride); a lower alkylamine such as methylamine, dimethylamine, ethylamine, isopropylamine, etc.; a lower alkenylamine such as allylamine, 2-butenylamine, etc.; a lower alkynylamine such as propargylamine, pentynylamine, etc.; and the like. Examples of the compounds of formula $III_2$ are lower alkylsulfonamide such as methansulfonamide, ethansulfonamide etc.; halogeno lower alkylsulfonamide such as trifluoromethanesulfonamide etc.; unsubstituted or substituted arylsulfonamide such as benzenesulfonamide, p-chlorobenzenesulfonamide, p-aminobenzenesulfonamide etc.; sulfamide; lower alkylsulfamide such as methylsulfamide, diethylsulfamide etc.; aryl-sulfamide such as phenylsulfamide, naphthylsulfamide etc.; aralkylsulfamide such as benzylsulfamide.

The reaction is usually performed in a solvent and suitable solvent include, for example, organic solvents

TABLE I

| | Pharmacological activities of $H_2$-blockers | | |
|---|---|---|---|
| Compound | (A) Gastric secretion $ED_{50}$ ($\mu$g/Kg i.v.) | (B) Pylorus-ligated rats $ED_{50}$ (mg/Kg i.d.) | (C) $LD_{50}$ (mg/Kg i.v.) in mice |
| Compound of this invention | | | |
| Example 1 (base) | 8.7 ± 0.5 | 0.87 (0.38–1.97) | 244.4 |
| Example 2 (base) | 19.1 ± 2.6 | 8.9 (3.8–20.8) | 152.1 |
| Known compound | | | |
| Compound A *1 (base) (Cimetidine) | 333.3 ± 42.0 | 42.6 (21.8–83.3) | 152.5 |
| Compound B *2 (base) | 35.2 ± 2.2 | 49.3 (26.0–93.5) | 94.6 |

*1 chemical name: N-cyano-N'-methyl-N''-{2-[(4-methyl-5-imidazolyl)methylthio]ethyl}guanidine (a typical compound of U.S. Pat. No. 3,950,333, only this compound is commercially sold)
*2 chemical name: 2-guanidino-4-[2-(2-cyanoguanidino)ethylthiomethyl]thiazole (a typical compound of Belgian Patent No. 866,156)

such as methanol, ethanol, isopropanol, chloroform, ether, tetrahydrofuran, benzene, etc. It is preferred that these solvents do not contain water. There is no particular restriction about the reaction temperature but the reaction is preferably performed at room temperature or under heating. Also, it is preferred that the reaction system be in a neutral to basic state.

Then, the process of this invention will further be explained by the following examples. In the examples, mp, Anal., NMR and Mass. are abbreviations for melting point, elementary analysis values, nuclear magnetic resonance spectrum and mass spectrum, respectively.

EXAMPLE 1

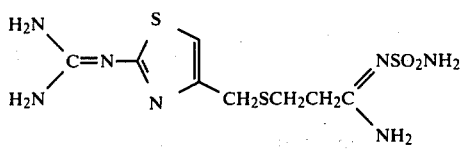

In 30 ml of methanol was dissolved 4.09 g of methyl 3-[(2-guanidinothiazol-4-yl)methylthio]propionimidate and then 15 ml of a methanol solution of 2.88 g of sulfamide was added to the solution under refluxing. After refluxing for about 3 hours, the solvent was distilled off under reduced pressure and the residue was purified by a silica gel column chromatography using a mixture of chloroform and methanol (20:1→10:1) as the developing solvent to provide 3,26 g of N-sulfamoyl-3-[(2-guanidinothiazol-4-yl)methylthio]propionamidine. The product shows the following physical chemical properties:

(i) Melting point: 163°–164° C.
(ii) Elemental analysis for $C_8H_{15}N_7O_2S_3$:

|  | C | H | N |
| --- | --- | --- | --- |
| Calculated: | 28.48% | 4.48% | 29.06% |
| Found: | 28.37% | 4.48% | 28.97% |

(iii) Nuclear magnetic resoance spectra (DMSO-$d_6$)
δ: 2.50 (2H, m, —SCH$_2$CH$_2$—), 2.65 (2H, m, —SCH$_2$CH$_2$—), 3,60 (2H, s,

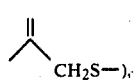

6.45 (1H, s,

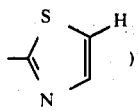

(iv) Mass spectrum: (FD method), m/e 338

In addition, methyl 3-[(2-guanidinothiazol-4-yl)methylthio]propionimidate used as the raw material in this example was prepared by the following method.

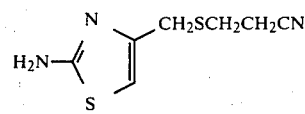

(a)

in a mixture of 490 ml of water and 320 ml of ethanol was dissolved 98.1 g of S-(2-aminothiazol-4-ylmethyl)isothiourea 2-hydrochloride (see, "J. Am. Chem. Soc.", 68, 2155–2159(1946)) in nitrogen stream and after adding thereto 37.0 g of chloropropionitrile, the mixture was cooled to 0°–10° C. and a solution of 45.1 g of sodium hydroxide in 450 ml of water was added dropwise to the mixture. Thereafter, the mixture was stirred for one hour at 0°–10° C. and further for one hour at room temperature and the product formed was extracted 4 times each with 600 ml of chloroform.

The chloroform layer obtained was washed with water and dried with anhydrous magnesium sulfate. Then, the solvent concentrated off under reduced pressure and the crystals deposited were collected by filtration to provide 47.2 g of 3-(2-aminothiazol-4-ylmethylthio)propionitrile showing a melting point of 104°–106° C.

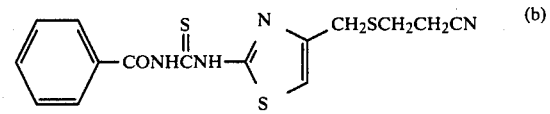

(b)

In 500 ml of acetone was dissolved 50 g of 3-(2-aminothiazol-4-ylmethylthio)propionitrile and after adding thereto 45 g of benzoyl isocyanate, the mixture was refluxed under heating for 5 hours. Thereafter, the solvent was concentrated off under reduced pressure and the crystals deposited were collected by filtration to provide 79.4 g of the needle crystals of 3-[2-(3-benzoylthioureido)thiazol-4-ylmethylthio]propionitrile showing a melting point of 158°–160° C.

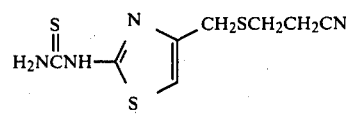

(c)

In a mixture of 1400 ml of acetone and 350 ml of methanol was dissolved 80 g of 3-[2-(3-benzoylthioureido)thiazol-4-ylmethylthio]propionitrile and after adding thereto a solution of 20 g of potassium carbonate in 300 ml of water, the mixture was stirred for 5 hours at 50° C. Then, the solvents were concentrated off under reduced pressure, the residue formed was added to 2,000 ml of ice water followed by stirring for 24 hours, and the crystals deposited were collected by filtration to provide 53.3 g of 3-(2-thioureidothiazol-4-ylmethylthio)propionitrile showing a melting point of 135°–137° C.

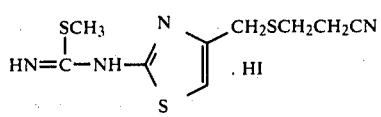

(d)

In 200 ml of ethanol was dissolved 15 g of 3-(2-thioureidothiazol-4-ylmethylthio)propionitrile hydroiodide and after adding thereto 12.4 g of iodomethyl, the mixture was refluxed under heating for one hour. Then, the solvent was concentrated off under reduced pressure and the crystals deposited were collected by filtration to provide 20.9 g of 3-[2-(S-methylisothioureido)-thiazol-4-ylmethylthio]propionitrile hydroiodide having a melting point of 148°–149° C. (decompd.).

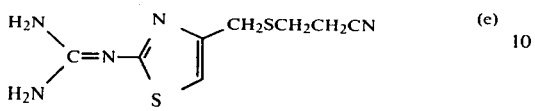
(e)

In 200 ml of methanol containing 17.0 g (1.0 mole) of ammonia were dissolved 20 g (0.05 mole) of 3-[2-(S-methylisothioureido)thiazol-4-ylmethylthio]propionitrile hydroiodide and 2.68 g (0.05 mole) of ammonium chloride and the solution was heated in a sealed tube to 80°–90° C. for 15 hours.

After cooling the reaction mixture, the solvent was distilled off under reduced pressure. To the residue obtained was added 200 ml of water and the mixture was made alkaline by the addition of a saturated aqueous solution of potassium carbonate. Then, the brown precipitates deposited were collected by filtration, air-dried, and recrystallized from acetone to provide 6.2 g of 3-(2-guanidinothiazol-4-ylmethylthio)propionitrile showing a melting point of 132° C.

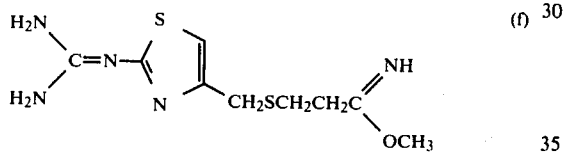
(f)

In a mixture of 60 ml of anhydrous methanol and 120 ml of anhydrous chloroform was dissolved 10 g of 3-(2-guanidinothiazol-4-ylmethylthio)propionitrile and after cooling the solution to 0°–10° C. in nitrogen stream and passing therethrough a dry hydrogen chloride gas for 3 hours, the solution was allowed to stand in a closed vessel at 0°–4° C. for 20 hours.

Then, the solvents were distilled off under reduced pressure and the concentrated residue was poured into 200 ml of ice-water containing 30 g of potassium carbonate, and the mixture solution was extracted three times with 150 ml of chloroform containing 20% methyl alcohol.

The organic layer was dried over anhydrous magnesium sulfate, and the solvent was distilled away under reduced pressure to provide 10.3 g of mehtyl-3-[(2-guanidinothiazol-4-yl)methylthio]propionimidate.

EXAMPLE 2

(a) In 10.2 ml of methanol were dissolved 1.27 g of methyl 3-[(2-guanidinothiazol-4-yl)methylthio]propionimidate and 0.86 g of methanesulfonamide and after reacting for 48 hours at room temperature, the solvent was distilled off under reduced pressure. Then, the residue formed was purified by a silica gel column chromatography using a mixture of chloroform and methanol (20:1→10:1) to provide 1.44 g amorphous N-methanesulfonyl-3-[(2-guanidinothiazol-4-yl)-methylthio]propionamidine. The product shows the following physicochemical properties:

(i) Nuclear magnetic resonance spectra (CD$_3$OD) δ: 2.58 (2H, d, —SCH$_2$CH$_2$—), 2.78 (2H, d, —SCH$_2$CH$_2$—), 2.91 (3H, s, —CH$_3$), 3,67 (2H, s,

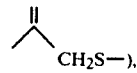
CH$_2$S—), 6.50 (1H, s,

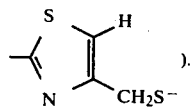
).

(ii) Mass spectrum (EI method): m/e 336.

(b) N-Methanesulfonyl-3-[(2-guanidinothiazol-4-yl)-methylthio]propionamidine thus obtained was dissolved in acetone and then an acetone solution of 0.5 g of maleic acid was added dropwise to the solution, thereby crystals deposited. The crystals were collected by filtration to provide N-methanesulfonyl-3-[(2-guanidinothiazol-4-yl)-methylthio]propionamidine maleate. The product shows the following physicochemical properties:

(i) Melting point: 195°–197° C.
(ii) Elemental analysis for C$_{13}$H$_{20}$N$_6$O$_6$S$_3$:

|  | C | H | N |
|---|---|---|---|
| Calculated: | 34.51% | 4.45% | 18.57% |
| Found: | 34.64% | 4.49% | 18.12% |

EXAMPLE 3

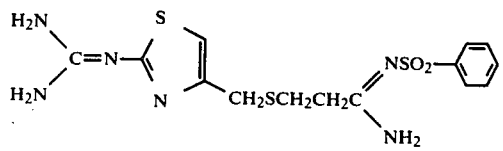

In 8 ml of methanol were dissolved 800 ml of methyl 3-[(2-guanidinothiazol-4-yl)methylthio]propionimidate and 590 mg of benzenesulfonamide and after causing reaction for 24 hours at room temperature, the solvent was distilled off under reduced pressure. The residue formed was purified by a silica gel column chromatography using a mixture of chloroform and methanol (20:1→10:1) to provide 855 mg of amorphous N-benzenesulfonyl-3-(2-guanidinothiazol-4-yl)methylthio propionamide. The product shows the following physicochemical properties:

(i) Nuclear magnetic resonance spectra (DMSO-d$_6$) δ:

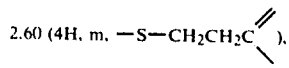
2.60 (4H, m, —S—CH$_2$CH$_2$C ), 3.55 (2H, s, 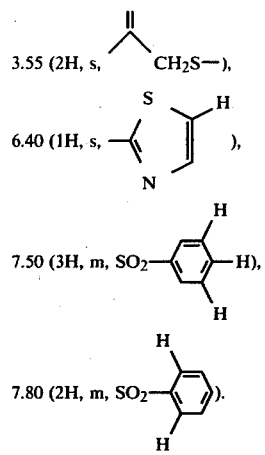 CH₂S—), 6.40 (1H, s, ...), 7.50 (3H, m, SO₂—⟨...⟩—H), 7.80 (2H, m, SO₂—⟨...⟩).

(ii) Mass spectrum (FD method): m/e 398

EXAMPLE 4

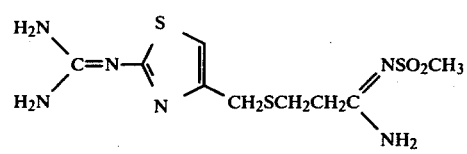

In 10 ml of methanol were dissolved 1 g of methyl 3-[(2-guanidinothiazol-4-yl)methylthio]propionimidate and 0.38 g of methanesulfonamide and after causing reaction for 48 hours at room temperature, the solvent was distilled off under reduced pressure. Then, the residue formed was dissolved in 3 ml of ethanol and the solution was allowed to cool, thereby white crystals deposited. The crystals were collected by filtration and dried to provide 0.7 g of N-methanesulfonyl-3-[(2-guanidinothiazol-4-yl)methylthio]propionamidine. The product shows the following physicochemical properties:

(i) Melting point: 117°–118° C.

Nuclear magnetic resonance spectra (CD₃OD) δ:

2.60 (2H, m, —SCH₂CH₂C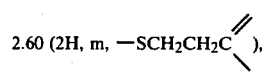), 2.80 (2H, m, —SCH₂CH₂C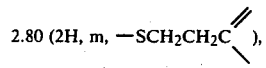), 2.92 (3H, s, SO₂CH₃), 3.66 (2H, s, 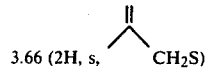 CH₂S)

6.50 (1H, s, 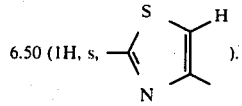).

EXAMPLE 5

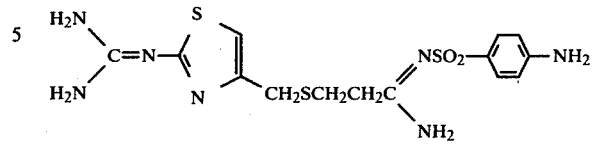

In 10 ml of ethanol were dissolved 1 g of methyl 3-[(2-guanidinothiazol-4-yl)methylthio]propionimidate and 0.69 g p-aminobenzenesulfonamide and after causing reaction for 48 hours at room temperature, the solvent was distilled off under reduced pressure. Then, the residue formed was purified by a silica gel column chromatography using a mixture of chloroform and methanol (20:1→10:1) to provide 1.2 g N-(p-aminobenzenesulfonyl)-3-[(2-guanidinothiazol-4-yl)methylthio]propionamidine as an amorphous solid. The product shows the following physicochemical properties.

Nuclear magentic resonance spectra (DMSO-d₆) δ:

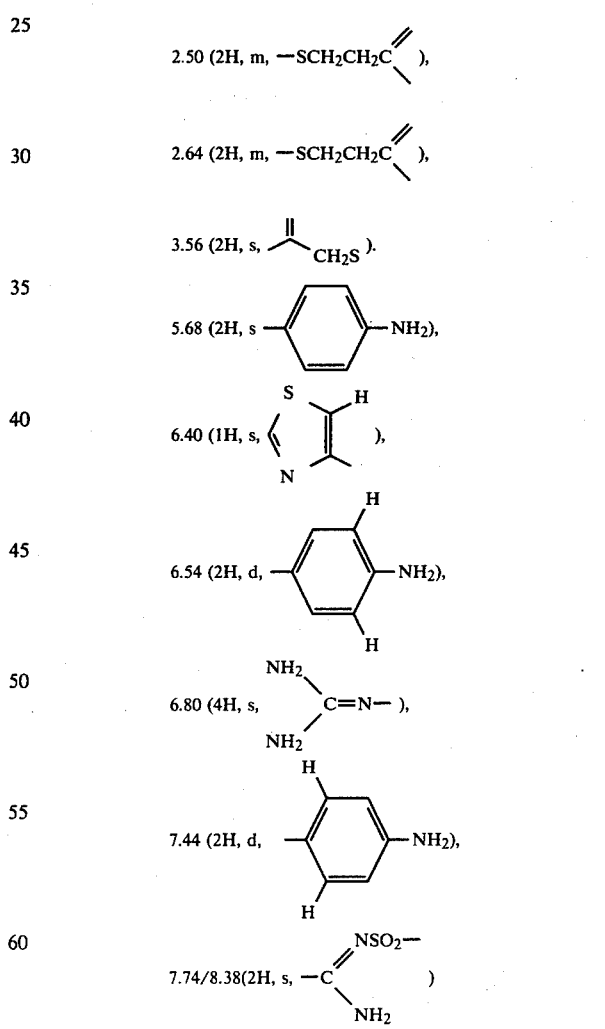

EXAMPLES 6–7

By following the same procedures as in Example 5, the following compounds were prepared.

EXAMPLE 6

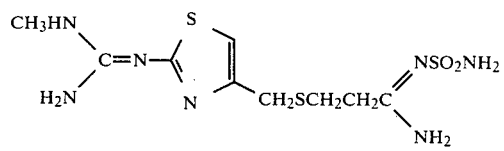

N-sulfamoyl-3-[(2-N-methylguanidinothiazol-4-yl)methylthio]propionamidine.

The amine used in the reaction: $H_2NSO_2NH_2$.
Physicochemical properties of the product:
(i) Melting point: 163°–164° C. (recrystallized from methanol).
(ii) Elemental analysis for $C_9H_{17}N_7O_2S_3$:

|  | C | H | N |
|---|---|---|---|
| Calculated: | 30.76% | 4.88% | 27.90 |
| Found: | 30.47% | 4.84% | 27.60% |

EXAMPLE 7

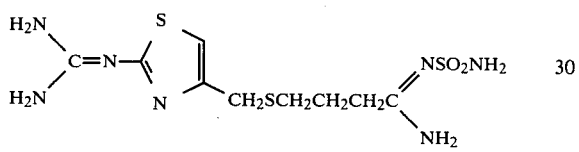

N-Sulfamoyl-4-[(2-guanidinothiazol-4-yl)methylthio]butyramidine.

The amine used in the reaction: $H_2NSO_2NH_2$.
Physicochemical properties of the product:
(i) Melting point: 159°–161° C. (recrystallized from ethanol).
(ii) Elemental analysis for $C_9H_{17}N_7S_3O_2$:

|  | C | H | N |
|---|---|---|---|
| Calculated: | 30.79% | 4.88% | 27.90% |
| Found: | 30.39% | 4.86% | 27.01% |

EXAMPLES 8–11

By following the procedure as in Example 2, the following compounds were prepared:

EXAMPLE 8

(a)

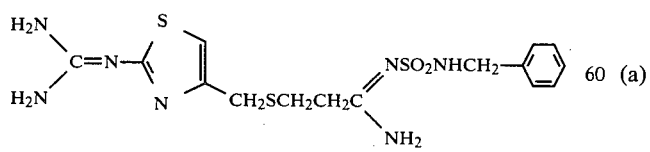

N-Benzylsulfamyl-3-[(2-guanidinothiazol-4-yl)methylthio]propionamidine.
(b) The maleate thereof.
The amine used for the reaction:

$H_2NSO_2NHCH_2$—⟨phenyl⟩

Physicochemical properties of the products:
(a)
(i) Nuclear magnetic resonance spectra (DMSO-$d_6$):

δ: 2.50 (2H, m, $SCH_2CH_2C$⟨), 2.64 (2H, m, $SCH_2CH_2C$⟨).

3.60 (2H, s, ⟨$CH_2S$— ), 4.02 (2H, d, $CH_2$—⟨phenyl⟩), 6.46 (1H, s, ⟨thiazole-CH_2S⟩), 6.82 (4H, s, ⟨guanidino C=N—⟩), 7.18 (1H, q, $SO_2NHCH_2$—⟨phenyl⟩), 7.24 (5H, s, ⟨phenyl-H⟩), 7.50, 8.30 (2H, s, —C(=N)NH_2 ).

(b)
(i) Melting point: 160°–162° C.
(ii) Elemental analysis for $C_{19}H_{25}N_7O_6S_3$:

|  | C | H | N |
|---|---|---|---|
| Calculated: | 41.98% | 4.64% | 18.04% |
| Found: | 41.79% | 4.64% | 17.90% |

EXAMPLE 9

(a)

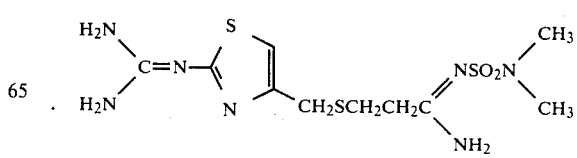

N-Dimethylsulfamyl-3-[(2-guanidinothiazol-4-yl)methylthio]propionamidine.
(b) The maleate thereof.
The amine used for the reaction:

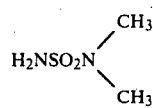

Physicochemical properties of the products:
(a)
(i) Nuclear magnetic resonance spectra (DMSO-$d_6$):

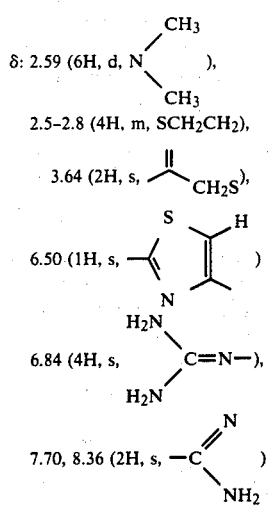

(b)
(i) Melting point: 183°–186° C.
(ii) Elemental analysis for $C_{14}H_{23}N_7O_6S_3$:

|  | C | H | N |
|---|---|---|---|
| Calculated: | 34.92% | 4.81% | 20.30% |
| Found: | 34.82% | 4.76% | 19.96% |

EXAMPLE 10

(a)

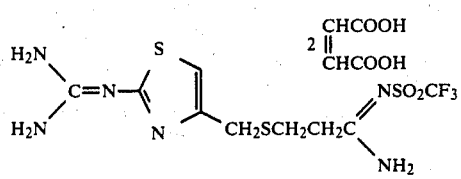

N-Trifluoromethanesulfonyl-3-[(2-guanidinothiazol-4-yl)methylthio]propionamidine maleate
The amine used for the reaction: $H_2NSO_2CF_3$
(i) Melting point: 168°–170° (recrystallized from methyl ethyl ketone)
(ii) Elemental analysis for $C_{17}H_{21}N_6O_{10}S_3F_3$:

|  | C | H | N |
|---|---|---|---|
| Calculated: | 32.80% | 3.40% | 13.50% |
| Found: | 32.70% | 3.46% | 14.00% |

EXAMPLE 11

(a)

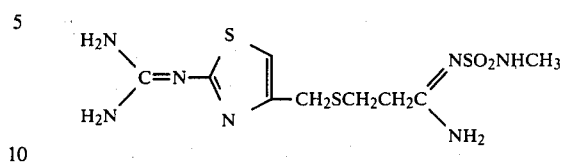

N-Methylsulfamyl-3-[(2-guanidinothiazol-4-yl)methylthio]porpionamidine.
(b) The maleate thereof.
The amine used for the reaction: $H_2NSO_2NHCH_3$.
Physicochemical properties of the products:
(a)
(i) Nuclear magnetic resonance spectra (DMSO-$d_6$):

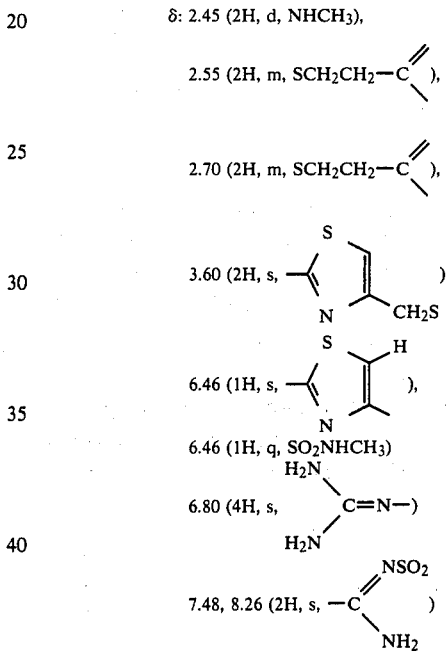

(b)
(i) Melting point: 181°–184° C.
(ii) Elemental analysis for $C_{13}H_{21}N_7O_6S_3$:

|  | C | H | N |
|---|---|---|---|
| Calculated: | 33.40% | 4.53% | 20.97% |
| Found: | 33.36% | 4.43% | 20.68% |

EXAMPLE A

Medical composition—tablet for oral administration.
Composition for 1,000 tablets:
Active component: 260 g.
Starch: 37 g
Milk sugar: 50 g
Magnesium stearate: 3 g.
The components shown above were granulated by an ordinary manner using starch paste as a binder and then molded into tables each having 9.5 mm diameter.

EXAMPLE B

Medical composition—formulation for injection

Composition for 2 ml of injection:
Active component: 260 mg
Distilled water for injection to make: 2 ml.

Distilled water for injection was added to the active component and the active component was dissolved while passing therethrough a nitrogen gas to provide a solution having a concentration of 13% (a concentration of 10% as a base). After filtering the solution by a bacterial filter, 2.2 ml each of the solution was poured in a 2 milliliter ampule under sterile state and after replacing the space in the ampule with nitrogen gas, the ampoule was sealed.

EXAMPLE 12

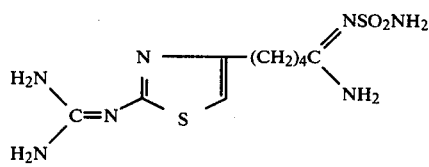

1.3 g of methyl 5-(2-guanidinothiazol-4-yl)pentanoimidate and 1.1 g of sulfamide were dissolved in 4.3 g of methanol, and the solution was allowed to stand overnight at room temperature. The solvent was distilled away under reduced pressure and the residue was purified by a silica gel column chromatography using a mixture of acetone and methanol as the developing solvent. The obtained crystals were dissolved in 0.4 ml of acetic acid, 4 ml of ehtanol and 8 ml of water, and the solution was treated with activated charcoal. To the filtrate was added 6.6 ml of N—NaOH, and the precipitated crystals were filtered off to provide 0.70 g of N-sulfamoyl-5-(2-guanidinothiazol-4-yl)pentanoamidine having a melting point of 156°–157° C.

Elemental analysis for $C_9H_{17}N_7O_2S_2$

|  | C | H | N |
|---|---|---|---|
| Calculated | 33.84 | 5.36 | 30.70 |
| Found | 33.55 | 5.45 | 30.24 |

What is claimed is:
1. Guanidinothiazole compounds of the formula

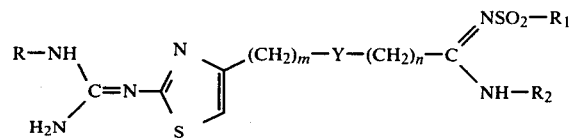

wherein R represents a hydrogen atom or a lower alkyl group, $R_1$ represents an amino group, a lower alkyl group, a halogeno lower alkyl group, a phenyl or naphthyl group which is unsubstituted or substituted by halogen, hydroxyl, amino, or alkoxy, a mono- or di-lower alkylamino group, an arylamino group or an aralkylamino group, $R_2$ represents a hydrogen atom, a lower alkyl group, a lower alkenyl group or a lower alkynyl group, Y represents a sulfur atom or a methylene group, m and n, each represents an integer of 1-3, and the pharmacologically acceptable acid addition salts thereof.

2. The compounds as claimed in claim 1 wherein R and $R_2$ are hydrogen atoms, $R_1$ is an amino group and Y is a sulfur atom.

3. The compounds as claimed in claim 1 wherein $R_2$ is a hydrogen atom or a lower alkyl group.

4. The compound as claimed in claim 1 which is N-sulfamoyl-3-[(2-guanidinothiazol-4-yl)methylthio]-propionamidine.

5. The compound as claimed in claim 1 which is N-methansulfonyl-3-[(2-guanidinothiazol-4-yl)methylthio]propionamidine.

6. Medical composition containing a gastric acid secretion inhibiting amount of a guanidinothiazole compound of the formula

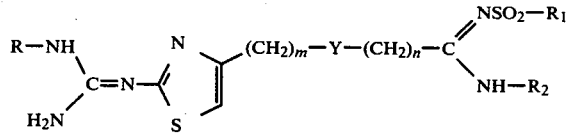

wherein R represents a hydrogen atom or a lower alkyl group, $R_1$ represents an amino group, a lower alkyl group, a halogeno lower alkyl group, a phenyl or naphthyl group which is unsubstituted or substituted by halogen, hydroxyl, amino, or akoxy, a mono- or di-lower alkylamino group, an arylamino group or an aralkylamino group, $R_2$ represents a hydrogen atom, a lower alkyl group, a lower alkenyl group or a lower alkynyl group, Y represents a sulfur atom or a methylene group, m and n, each represent an integer of 1-3, or a non-toxic acid addition salt thereof and pharmaceutically acceptable carriers or diluents.

* * * * *

UNITED STATES PATENT AND TRADEMARK OFFICE
CERTIFICATE OF CORRECTION

PATENT NO. : 4,283,408

DATED : August 11, 1981

INVENTOR(S) : Hirata et al.

It is certified that error appears in the above-identified patent and that said Letters Patent is hereby corrected as shown below:

Column 16, line 47: change "akoxy" to --alkoxy--

Signed and Sealed this

Eleventh Day of February 1986

[SEAL]

Attest:

DONALD J. QUIGG

Attesting Officer

Commissioner of Patents and Trademarks

UNITED STATES PATENT AND TRADEMARK OFFICE

CERTIFICATE EXTENDING PATENT TERM
UNDER 35 U.S.C. 156

Patent No.   : 4,283,408

Dated        : August 11, 1981

Inventor(s)  : Yasufumi Hirata, et al

Patent Owner : Yamanouchi Pharmaceutical Co., Ltd.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this First day of October 1987.

Donald J. Quigg

Assistant Secretary and Commissioner of Patents and Trademarks